United States Patent [19]
Hamelin et al.

[11] Patent Number: 5,804,964
[45] Date of Patent: Sep. 8, 1998

[54] WIRE ROPE DAMAGE INDEX MONITORING DEVICE

[75] Inventors: Michel Hamelin, St-Lazare; Frank Kitzinger, Montreal, both of Canada

[73] Assignee: Noranda Inc., Toronto, Canada

[21] Appl. No.: 757,668

[22] Filed: Nov. 29, 1996

[51] Int. Cl.[6] .......................... G01N 27/82; G01N 27/83; G01R 33/12
[52] U.S. Cl. .......................... 324/242; 324/227; 324/235
[58] Field of Search ..................................... 324/206, 227, 324/229, 232, 235, 238, 240–242

[56] References Cited

U.S. PATENT DOCUMENTS

| | | | |
|---|---|---|---|
| 4,096,437 | 6/1978 | Kitzinger et al. | 324/227 |
| 4,445,088 | 4/1984 | Schubel | 324/240 X |
| 4,495,465 | 1/1985 | Tomiauolo et al. | 324/232 |
| 5,036,277 | 7/1991 | van der Walt | 324/235 |
| 5,402,066 | 3/1995 | Hickman, Jr. et al. | 324/232 X |
| 5,414,353 | 5/1995 | Weischedel | 324/232 |
| 5,565,771 | 10/1996 | Hamelin et al. | 324/225 |

OTHER PUBLICATIONS

Weischedel H.R., *Mining Science and Technology*, 1990, 11, 85–93.
Kuun et al., "Condition assessment of winding ropes", presented at the 2nd International Conference on Mine Hoising, London, England, Jun. 28–30 1993.

*Primary Examiner*—Gerard R. Strecker
*Attorney, Agent, or Firm*—Fitzpatrick, Cella, Harper & Scinto

[57] ABSTRACT

A magnetic testing device for obtaining a damaged index of an elongated magnetically-permeable object in real time includes a permanent magnet assembly with spaced-apart poles, a tubular pole piece adapted to surround the object, Hall effect devices placed in the magnetic flux path, a leakage flux sensor installed between the pole pieces, and a real time signal processing unit. The signal processing unit provides local fault (LF) signals generated by the leakage flux sensor, and loss of metallic area (LMA) signals generated by the Hall effect devices. The standard deviations of the LF signals are summed, the root-mean-square of the LF signals is summed, the absolute values of the LF signals are integrated, and the LMA signal is multiplied by a coefficient which is dependent on the object construction. The damage index is then determined using the thus-calculated values. Preferably, when a wire rope is passed through the monitoring device, the damage index is given to the user in a hand-held display means. Preferably, no interpretation is required by the user.

10 Claims, 8 Drawing Sheets

WIRE ROPE DAMAGE INDEX MONITORING DEVICE

FIELD OF THE INVENTION

The present application is concerned with a device for monitoring the damage condition of elongated ferromagnetic objects like wire ropes. The latter are passed into the device and a damage index, characteristic of the wire rope's condition, is displayed on portable display means attached thereto.

BACKGROUND OF THE INVENTION

Several instruments have been developed for the inspection and nondestructive testing (NDT) of wire ropes. Conventionally, these instruments use electromagnets or permanent magnets that induce a magnetic flux in the wire ropes, and measurement of the flux leakages or variations in the magnetic flux path allow one to locate the deficiencies in the wire ropes. Flux leakages are generally caused by local faults, such as nicked or broken wires, while variations in the amount of flux passing through the wire rope are the result of loss of metallic area due to wear, corrosion and the like.

Current testers operate in the following manner: the elongated object is passed through the tester containing a first set of sensors located between the poles of the magnet, and adapted to detect flux leakages caused by local faults. A second set of sensors in the main flux path are measuring flux variations caused by loss of metallic area. Two signals, namely the local fault signal (LF) and loss of metallic area signal (LMA), are therefore generated. An example of such tester is disclosed and claimed in U.S. Pat. No. 4,096,437, which is hereby incorporated by reference.

The major drawbacks associated with this tester are that each of the LF signal and the LMA signal must be interpreted according to the physical characteristics of the sensing head. Furthermore, the LF signal only serves qualitative purposes because it varies with the spatial derivative of the leakage flux as measured by the LF sensors. To solve the resolution problem, means for increasing the linear resolution of the metallic area measurement of the object have been added, thus giving a signal corresponding more closely to the variations in the metallic area of the elongated object. This improvement is disclosed in U.S. Pat. No. 5,565,771.

Although the above instruments provide excellent and reliable results, they are sometimes substituted by a rapid visual inspection, particularly for shorter wire ropes. However, since more and more wire ropes are embedded in polymeric envelopes to prevent corrosion and reduce wear, proper visual inspection of such embedded wire ropes are virtually impossible. Visual inspection is only possible for the outer, plastic covered surface, and defects within the wire rope cannot therefore be detected.

Accordingly, there is a need for a simple, handy, portable wire rope damage monitoring device overcoming the above limitations. Such device should give a damage index indicating the defects or degree of wear of the wire rope and be versatile enough to be used by anyone. The device should also be preferably less expensive than the previous instruments developed for that purpose.

SUMMARY OF THE INVENTION

In accordance with the present invention, there is now provided a magnetic testing device for obtaining a damage index of an elongated magnetically permeable object in real time, the device comprising:

i) a permanent magnet assembly having poles adapted to be spaced apart in the longitudinal direction of an elongated ferromagnetic object for inducing a longitudinal magnetic flux in a section of the object between the poles of the magnet assembly, the magnet assembly being strong enough to magnetically saturate the section of the object;

ii) a tubular pole piece adapted to surround the object adjacent each pole of the permanent magnet assembly for directing the magnetic flux radially into the object at one pole and out of the object at the other pole;

iii) Hall effect devices placed in the path of the magnetic flux for sensing the reduction of the flux passing through the elongated object due to any reduction of cross-sectional area of the elongated object between the pole pieces caused by loss of metallic area in the elongated object;

iv) a leakage flux sensor installed between the pole pieces for detecting external and internal defects in the objects; and v) a real time signal processing unit for
   a) length referencing local fault (LF) and loss of metallic area (LMA) signals by digitally sampling along the object length at preset distance intervals;
   b) summing of standard deviations of LF signals;
   c) summing of the root-mean-square of the LF signals;
   d) integrating the absolute values of the LF signal;
   e) multiplying the LMA signal by a rope construction dependent nonlinear coefficient; and
   f) solving a damage index equation by application of values obtained in steps b, c, d, e, whereby a numerical damage index based on wire rope damage mechanics is obtained.

In a preferred embodiment, the damage index equation is $$D_i = A(y)y \sqrt{ \sigma(x_i \ldots x_{i+m}) \int (x_i \ldots x_{i+n})^2 dx }$$

wherein

"i" is the current data point index;

"m" is the number of data points included in the longitudinal resolution of the instrument;

"n" is the number of data points included in the two-laylength integrating length;

"$D_i$" is the damage index at the location of the $i^{th}$ data point;

"$x_i$" is the $i^{th}$ LF data point;

"$y_i$" is the $i^{th}$ LMA data point;

"A(y)" is the nonlinear LMA-dependent coefficient;

"σ( ... )" is the standard deviation of data set; and

"∫( ... )" is the numerical integration of data set.

Further, a smoothing window comprising a set of weighing coefficients to the LF data set is preferably applied before solving the damage index equation.

DETAILED DESCRIPTION OF THE INVENTION

The monitoring device of the present invention uses similar sensing means and methods as those in more sophisticated wire rope testers, namely Hall-effect sensors measuring loss-of-metallic-area (LMA) and local fault (LF) signals. But instead of supplying a continuous analog signal as for the instruments in U.S. Pat No. 4,096,437 and U.S. Pat. No. 5,565,771, the output is now an accurately rope-length referenced digital data stream. Typically, numerical values of LF and LMA data are produced every 2 millimeters. In reality, a digital signal from a rope driven wheel encoder is used to trigger the sampling circuit of an analog to digital converter. The resulting length-referenced base signals make it possible to obtain a true damage index by processing the data in real time. The present device is specifically designed to provide low cost, simple operation to users of plastic-enhanced and conventional wire ropes. Typical applications include testing crane ropes in plants, ship yards and at construction sites. An important advantage of the present monitoring device resides in a hand-held readout unit that uses digital signal processing (DSP) technology to process the data in real time and displays a damage index relating to the general degradation state of the rope under test.

Figure 1:
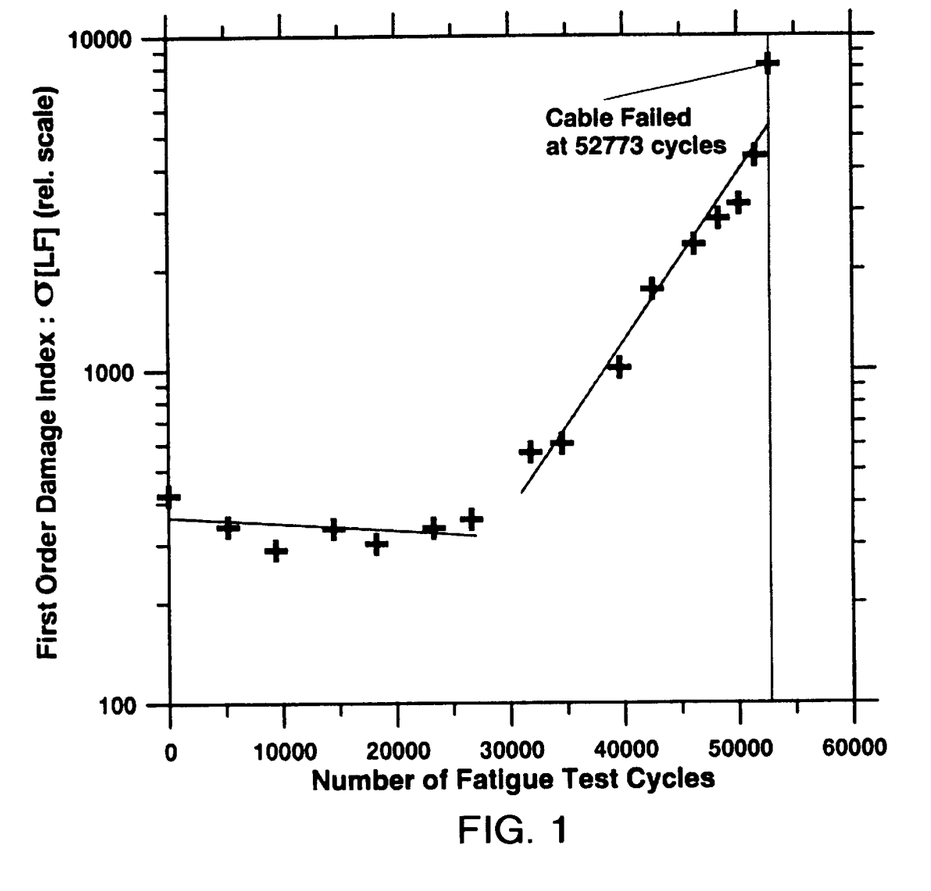
FIG. 1 illustrates the variations in standard deviation during a fatigue test for a ¾ in. diameter cushion core wire rope made of 6 strands comprising 25 wires each.

To demonstrate the present device, the changing rope conditions of ¾ inch diameter wire ropes of various construction were monitored during long term fatigue testing. An example of the results obtained is illustrated in FIG. 1. Fatigue testing simulates normal use of wire ropes in an accelerated fashion. The information collected during these tests led to the development of an original method for computing a damage index that provides a good indication of the degradation of the rope, while correcting errors due to factors such as the mutual interaction of neighbouring wire breaks.

The fatigue test consisted in cycling the wire rope around a sheave until breaking occurs, the wire rope being submitted to a load of approximately ⅓ of the nominal breaking strength. During the test, length referenced LMA and LF signals were recorded by the present monitoring device from the start until the wire rope broke. The data were then analyzed and different computation formulas were developed to obtain a damage index related to the true degradation of the rope. The results demonstrated that the rope degradation due to fatigue can be quantified by using signal processing techniques.

The first approximation of a damage index was computed by taking the standard deviation of the LF signal measured by the present device over a moving window corresponding approximately to one lay length of the rope. This approximation gave promising results in terms of gaining the capability to predict the rope failure, as illustrated by the standard deviations measured in FIG. 1. This approach takes into consideration a basic law of rope damage mechanics. The breaking strength loss caused by a single broken wire is gradually diminishing as we move away from the wire break. This effect is caused by friction between the individual wires constituting the wire rope. When multiple wire breaks happen within one lay length for example, friction cannot diminish the effect and the strength losses caused by several wires add up. The standard deviation of the LF signal varies with the severity of individual wire breaks and if they are closely grouped, such as within the moving window, their amplitude values should be summed to represent true damage conditions.

Figure 2A:
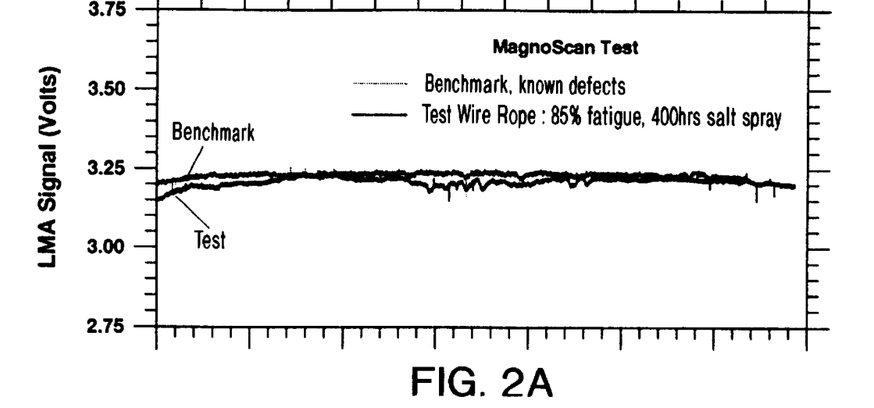
FIG. 2 illustrates the LMA signal, the LF signal and the standard deviation of the LF signal for two 6×25 stranded wire ropes, one being a benchmark new wire rope with known faults added thereto, and one being a test wire rope submitted to fatigue testing and corrosion testing.
Figure 2B:
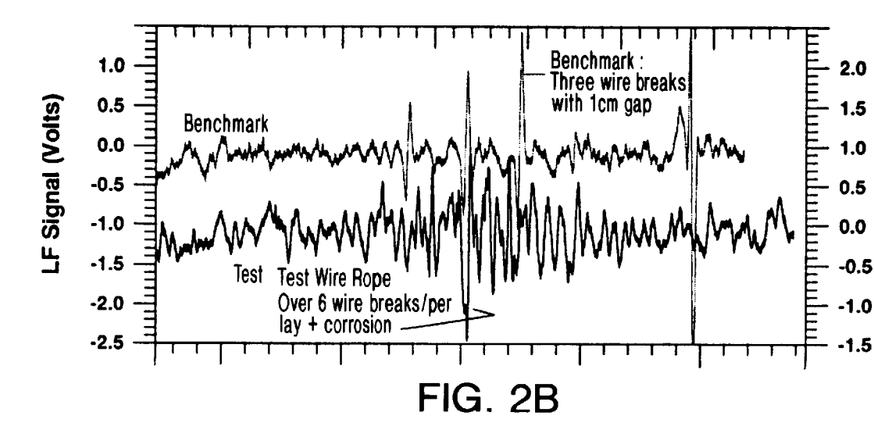
Figure 2C:
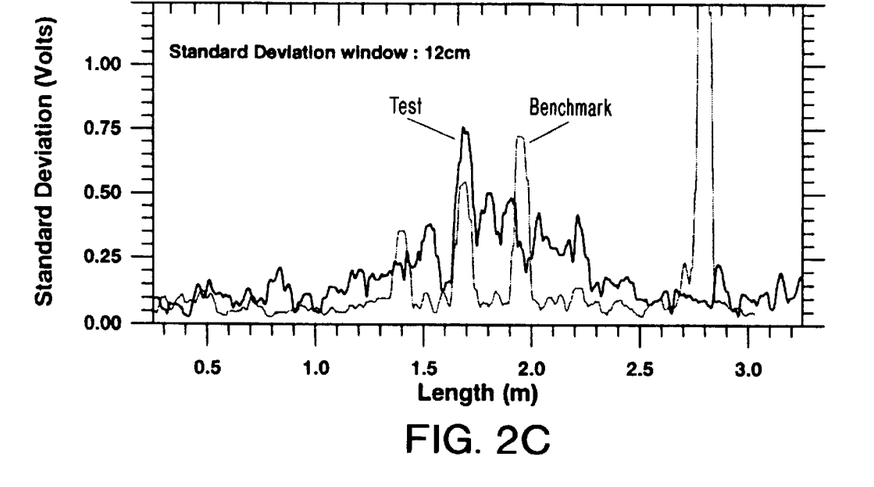

When testing wire ropes showing more complex degradation mechanisms like large concentration of wire breaks or corrosion, phenomena like mutual interaction of neighbouring defects become significant and cause interpretation errors. Mutual interaction of neighbouring defects is a well-known fact to those skilled in the art of nondestructive testing equipment. FIG. 2 shows an example of such interactions. The signals illustrated with a dark line were obtained from a wire rope placed beforehand in a corrosive environment for about 400 hours and therefore showed a more complex variety of defects than a second wire rope illustrated with a shaded line, having known defects such as broken wires. The LF signals obtained for both ropes are shown in FIG. 2b. It is apparent from FIG. 2c that taking the standard deviation of the LF signal alone does not properly represent the degradation state of the rope, i.e., the damage index should have a higher value in the section corroded and containing 6 wire breaks than in the section with only 3 wire breaks and no corrosion. In FIG. 2c, they are approximately equal. FIG. 2a shows the LMA signal for the same ropes. The standard deviation by itself is an insufficient way of computing this type of wire damage. To solve this problem, it has been found that part of the signal processing formula has to counteract the mutual interaction of neighbouring defects.

Figure 3:
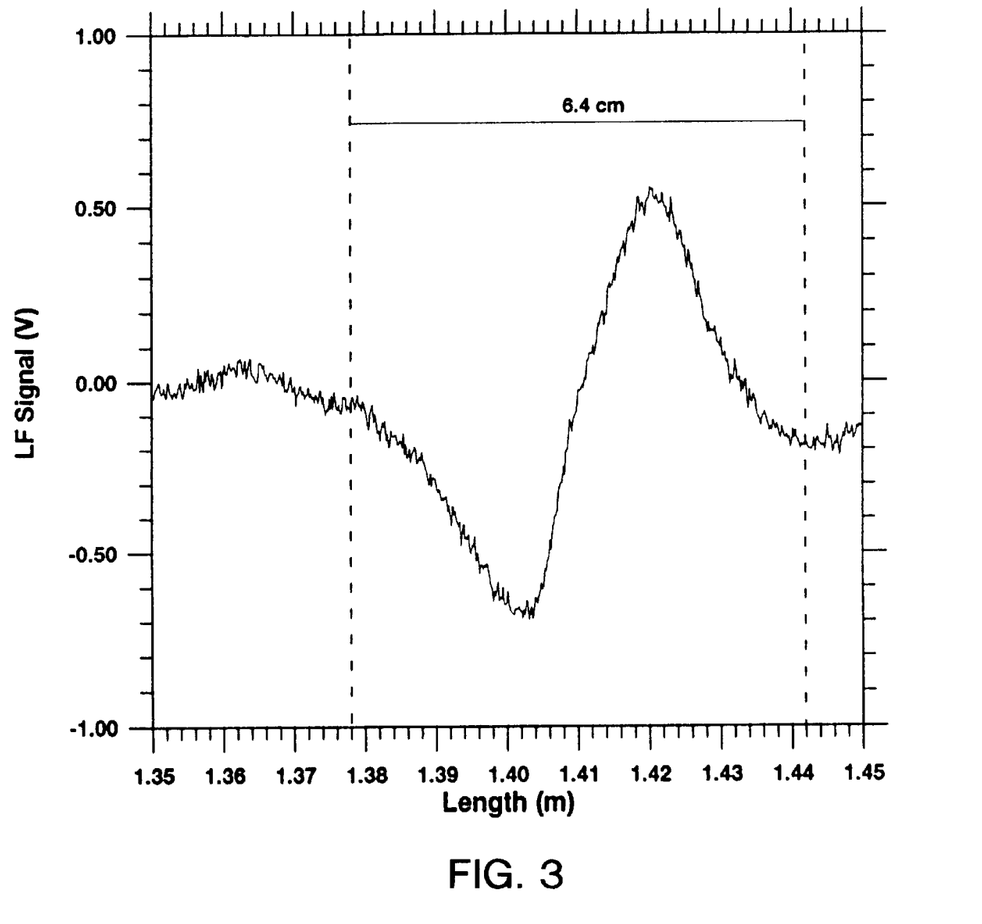
FIG. 3 illustrates the characteristic length of a single wire break as measured by the present monitoring device. This characteristic length is used as a base for calculating the standard deviation of the LF signal in the damage index computation.

In an advanced form of damage index computation, the standard deviation of the LF signal is computed over a wire rope length window representing the longitudinal resolution of the instrument. For example, as illustrated in FIG. 3, the monitoring device used has a length of 6 cm. This parameter or value is multiplied by the integral of the absolute value of the signal computed over a larger window which represents the length necessary to eliminate the interaction between two defects. This requires generally 2–3 lay lengths.

Figure 4A:
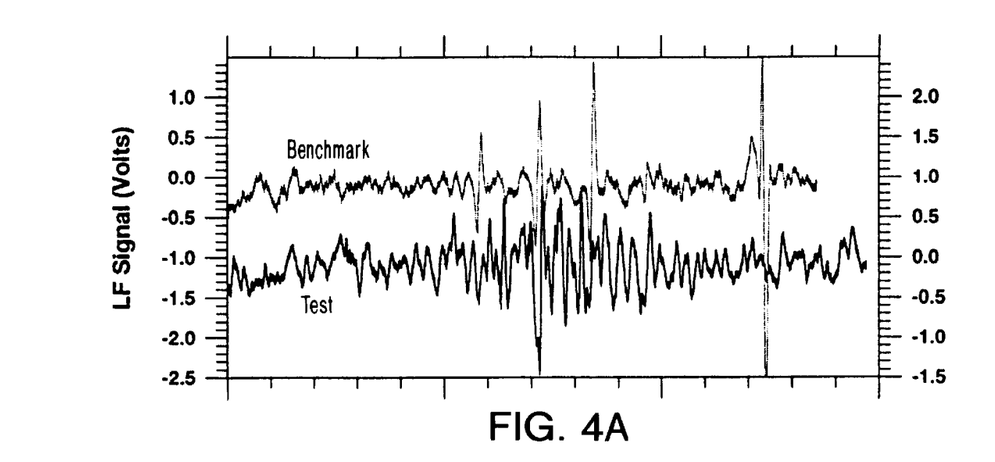
FIG. 4 illustrates the final result of the damage index computation for the benchmark and test wire ropes referred to in FIG. 2.
Figure 4B:
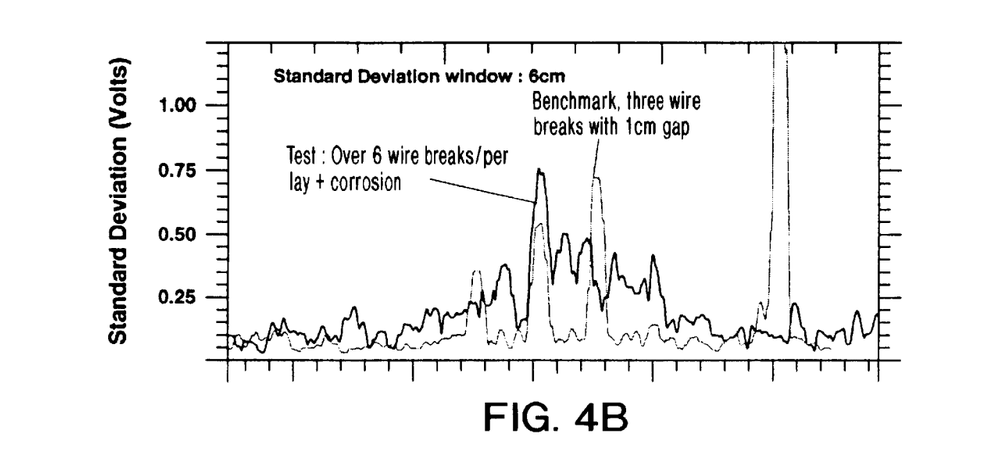
Figure 4C:
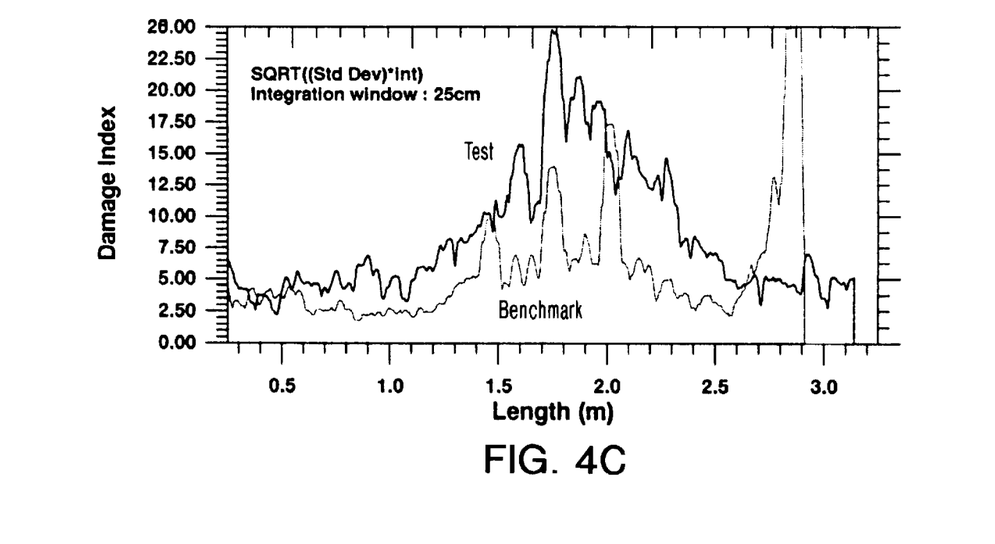

The result of this calculation for the wire ropes previously analyzed in FIG. 2 is illustrated in FIG. 4. It can be seen that, as expected, the wire rope showing more damage has a higher damage index. This computation method takes into consideration the increased signal variations due to a high concentration of local faults. In its final form, the damage index is further refined by multiplying the result with the LMA value in percentage scaled with a nonlinear coefficient. This index can then be calibrated against field test data. The resulting damage index can finally be expressed by the equation:

$$D_i = A(y) y \sqrt{ \sigma(x_i \ldots x_{i+m}) \int (x_i \ldots x_{i+n})^2 dx }$$

wherein:

"i" is the current data point index;

"m" is the number of data points included in the longitudinal resolution of the instrument For example, with a 6 cm resolution and a sampling rate of 1 data/2 mm, then m=30;

"n" is the number of data points included in the two-laylength integrating length. For example, with an integrating length of 25 cm and sampling rate of 1 data/2 mm, then n=125;

"$D_i$" is the damage index at the location of the $i^{th}$ data point;

"$x_i$" is the $i^{th}$ LF data point;

"$y_i$" is the $i^{th}$ LMA data point;

"A(y)" is the nonlinear LMA-dependent coefficient;

"$\sigma(\ldots)$" is the standard deviation of data set; and

"$\int(\ldots)$" is the numerical integration of data set.

Figure 5:
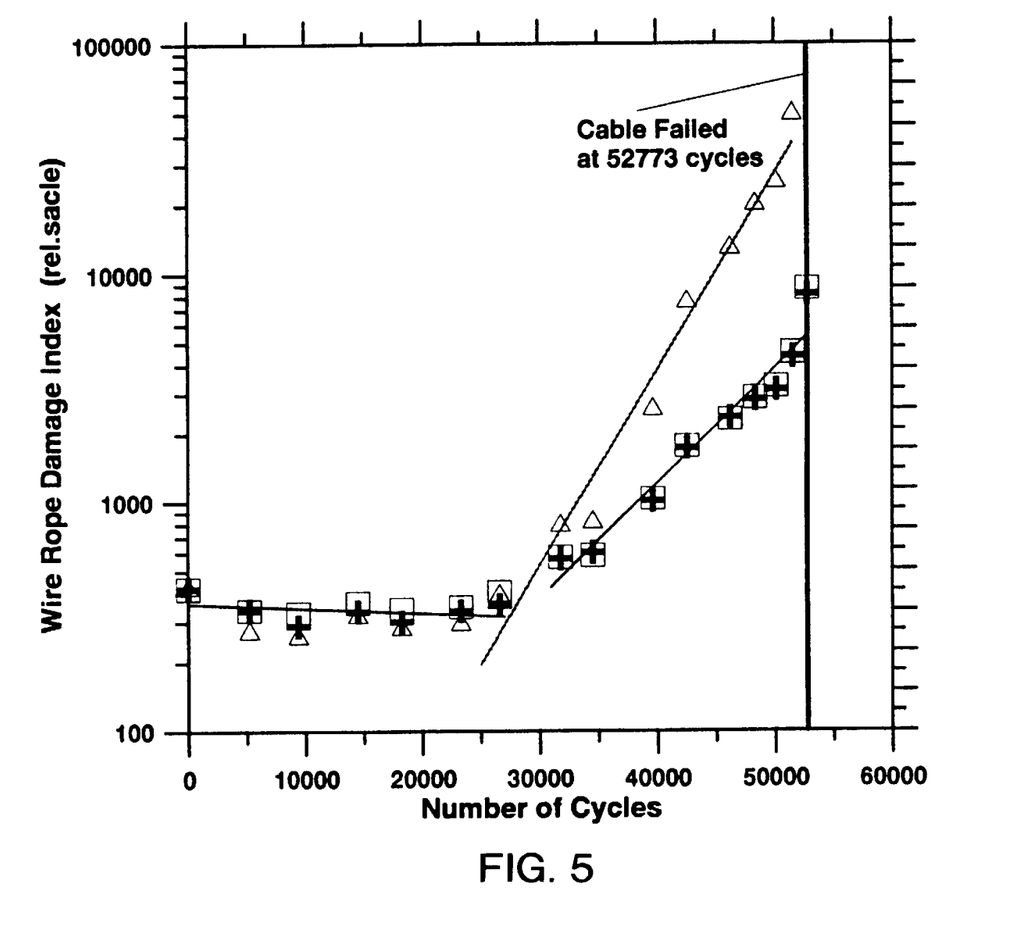
FIG. 5 illustrates the damage index versus the number of cycles for the wire rope referred to in FIG. 1.

FIG. 5 shows the new damage index (□) computed over the life of a wire rope submitted to fatigue life testing conditions as described supra. It can be seen that, when the rope is affected by broken wires only, both damage indexes, namely standard deviation (+) and standard deviation times integral (Δ), give similar results once properly scaled. The resulting real time damage index calculation follows the complex interaction of various laws of rope damage mechanics and corrects for known deficiencies of electromagnetic wire rope testing.

A further refinement can be implemented in the damage index calculation to take into account the effect on the strength of a wire of the distance between the measurement position and the position of a break in the wire. The effect of internal friction in the rope and the resulting "effective length" of a broken wire defined as the length over which the loss-of-strength of the broken wire disappears, has been studied extensively. The important aspect of this phenomenon as far as electromagnetic testing is concerned is that the maximum load that a single wire can carry will increase gradually from zero, at the break point, to eventually reach the original maximum load after a length called "effective length." To fully take this effect into account in the damage index computation, a smoothing window, i.e., a set of weighing coefficients, can be applied to the LF data points over the "effective length" before the numerical integration. This will give appropriate importance to defects at different distances, i.e., more importance to closely spaced defects and less importance to defects located at greater distances. The application of smoothing windows is a common practice in digital signal processing. For example various windows (hamming, blackman, exponential, etc.) have been developed to reduce the end effects in Fourier transforms and filtering applications.

Figure 6:
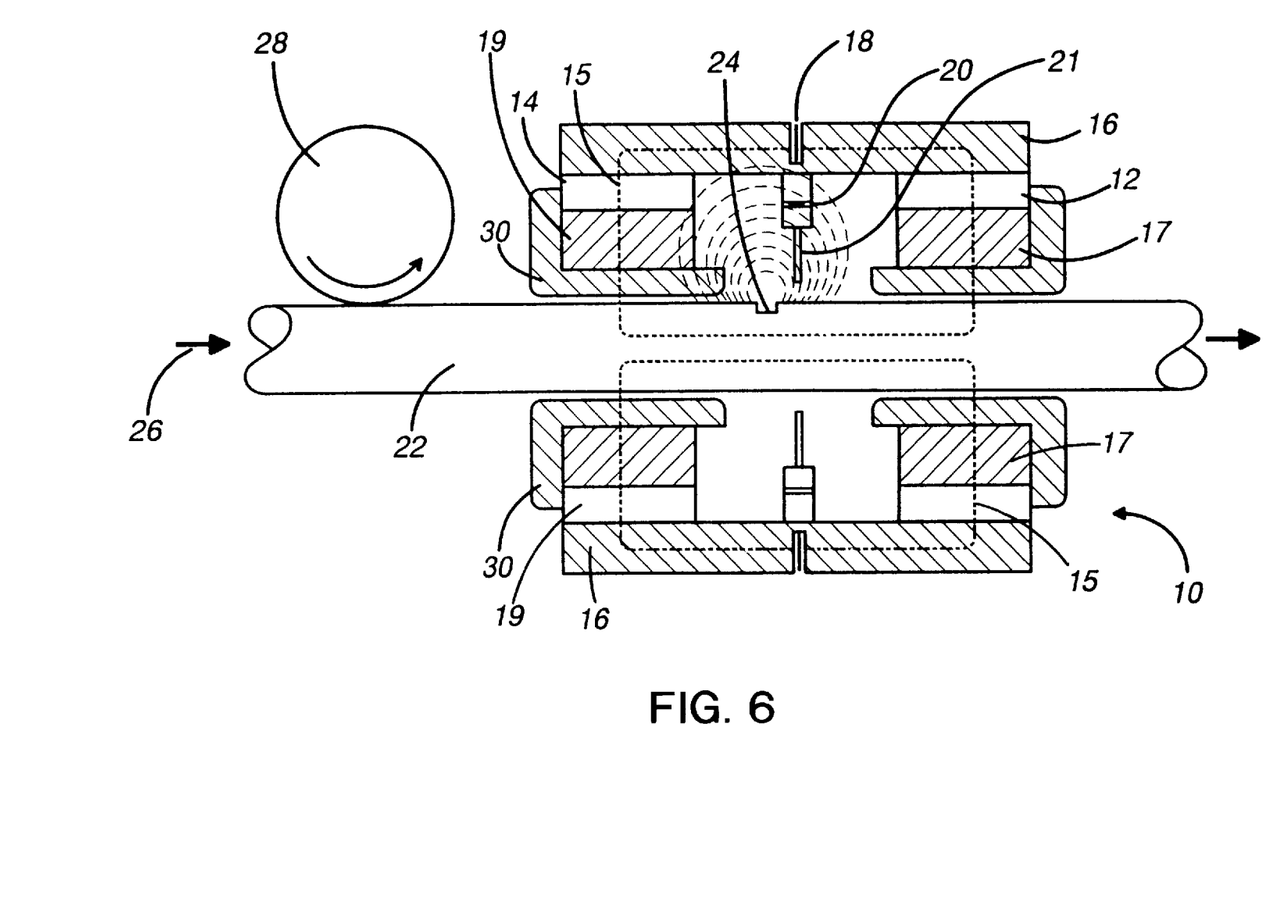
FIG. 6 illustrates a cross-sectional view of the sensor head of the present monitoring device.
Figure 8:
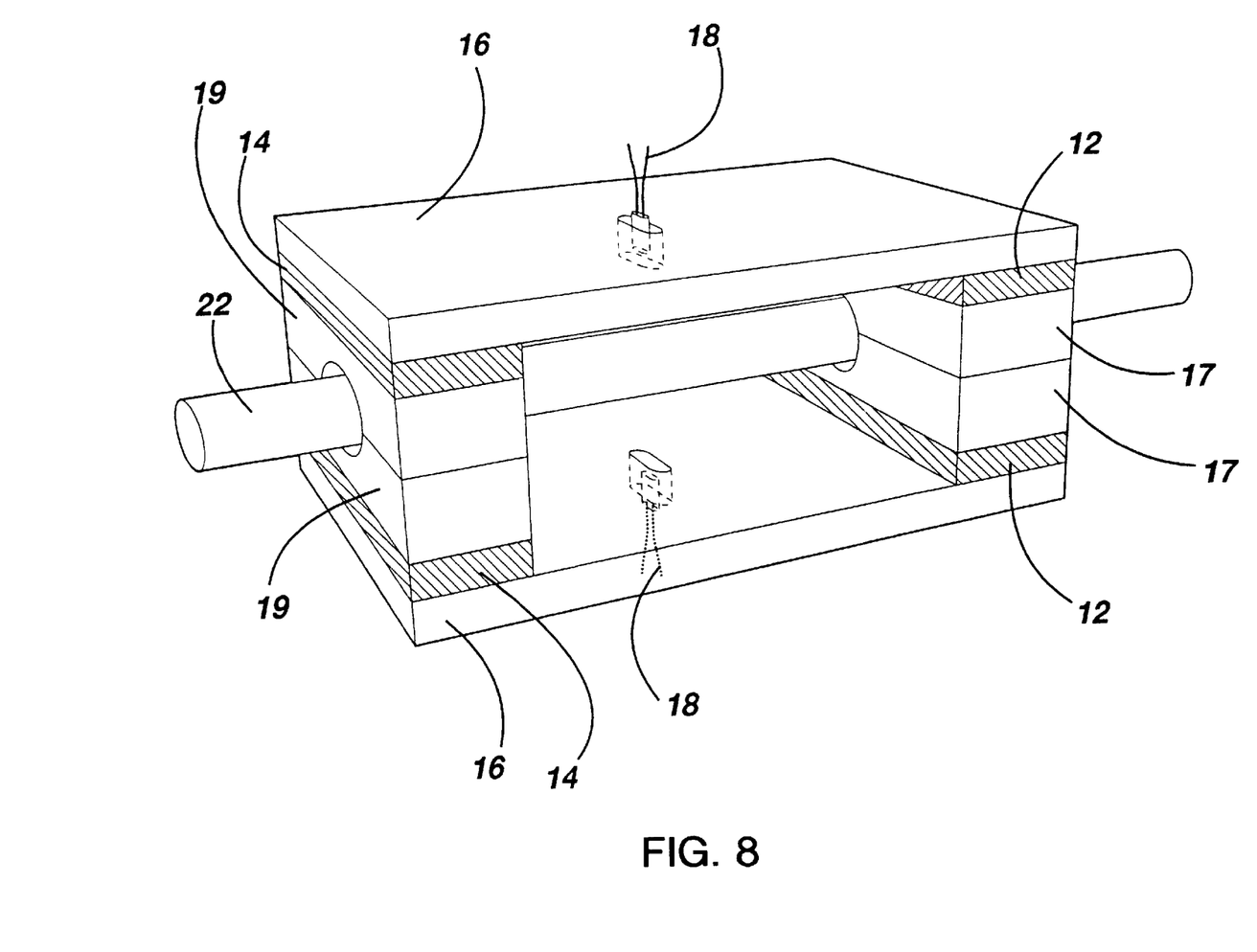
FIG. 8 illustrates a perspective view of the sensor head of the present monitoring device.

With respect to the sensor head, a preferred embodiment is illustrated in FIGS. 6 and 8. More specifically, tester 10 comprises magnets 12 and 14, having flux paths indicated by dashed lines 15 passing through tubular pole pieces 17 and 19, wire rope 22 and flux return bars 16. The dimensions of the tester are chosen to prevent magnetic saturation of bars 16 and pole pieces 17 and 19, but at the same time ensure magnetic saturation of the tested wire rope 22. Loss of metallic area sensors 18 are placed within bars 16. Local fault sensors 20 are positioned midway between poles 17 and 19, and coupled to leakage flux collectors 21. In operation, a wire rope 22 comprising one or more faults 24 is advanced into tester 10 in the direction indicated by arrows 26. Tester 10 further comprises a length transducer 28 for length referencing the wire rope faults. Guides 30 are also present to facilitate the passage of wire rope 22 therein. It should be noted that faults 24 can be either on the surface or inside wire rope 22.

Figure 7:
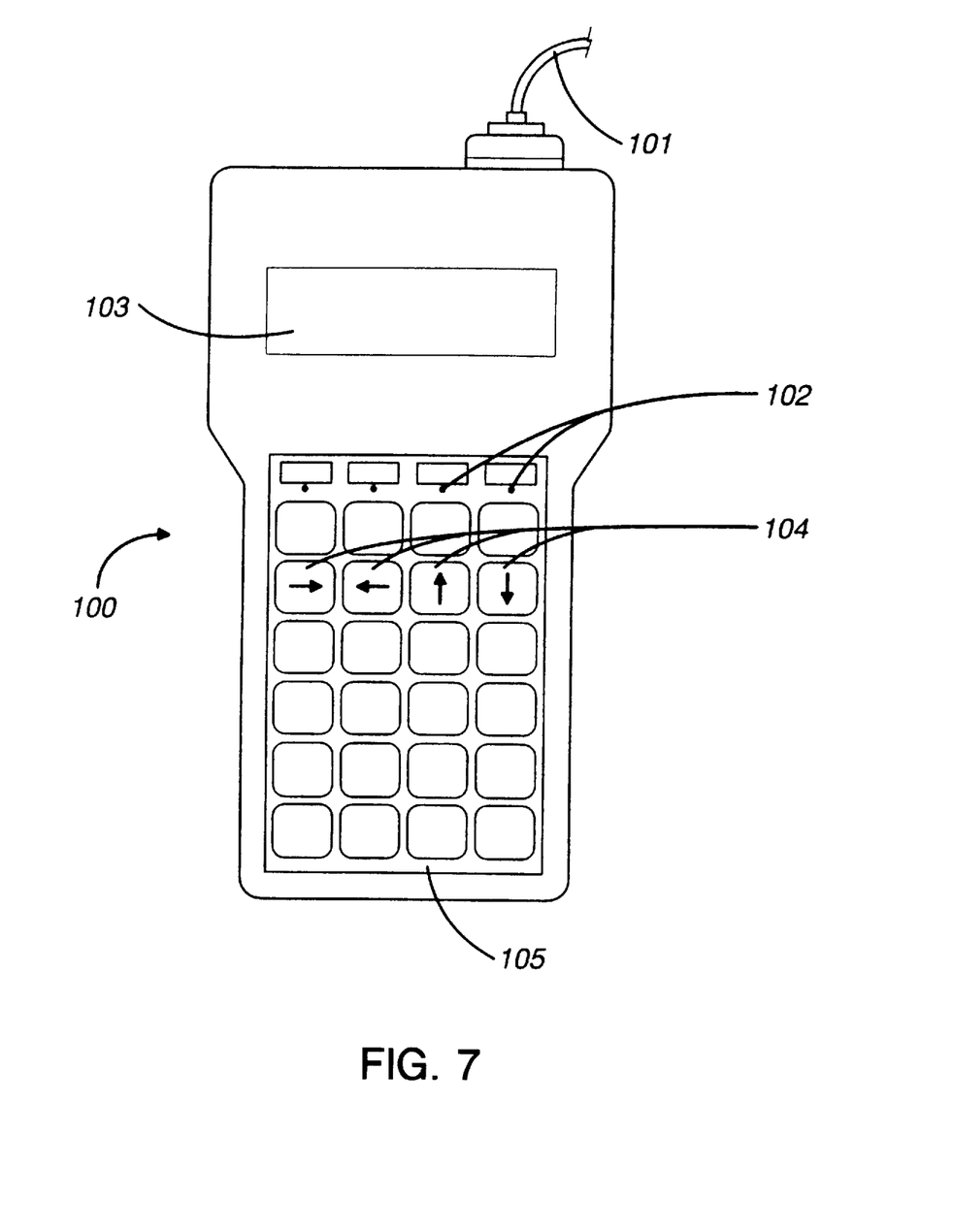
FIG. 7 illustrates the portable operator unit used together with the sensor head for processing and presentation of the data.

The signals corresponding to Local Faults and Loss-of-Metallic-Area are connected to the hand-held operator unit 100 illustrated in FIG. 7 with ordinary shielded copper wires 101. The operator unit 100 comprises an analog-to-digital converter which transmit the LF and LMA data in digital form to a Digital Signal Processor (DSP). The DSP is an electronic processor specifically designed to do mathematical computation in real time on continuously incoming data stream. The DSP solves in real time the damage index equation and puts in Random Access Memory (RAM) the damage index value for each section of wire rope 22. During the measurement, an alarm 102 lights up to indicate damaged sections of the wire rope. The alarm threshold can be modified by the user to correspond to a desired value of the damage index. At the end of a measurement, the damage index is displayed in a table form on the unit display 103. The user can scroll through the data with the help of arrow keys 104 on the unit keypad 105. The other keys of keypad 105 are used to modify parameters of the damage index computation. The user also has the possibility to link the portable operator unit to a printer to obtain print-outs of the results in table form.

The present monitoring device therefore has the following advantages over known testers:

it provides an instant wire rope damage index instead of LMA and LF signals. The damage index is a single number that quantifies various types of defects in the rope and is therefore more directly related to the loss-of-strength of the wire rope;

it uses established laws of wire rope failure mechanics, i.e., effective length of broken wire and mutual interaction between neighbouring defects, to compute the damage index;

it uses a different processor for signal processing and operator interface. The operator interface is hand-held, displays damage index numbers and their location along the length of the tested wire rope, includes alarm lights to indicate bad sections and may be coupled to a small field printer;

it records data in table form (damage index vs. position) instead of charts or graphs thus simplifying data presentation; and it is portable, does not require an experienced operator to handle it efficiently and provides quick and accurate indication on the state of the rope tested.

It is possible to use the signal processing techniques and damage index computation with other wire rope testers such as those described in U.S. Pat No. 4,096,437 and U.S. Pat. No. 5,565,771 but this requires adaptation of the software to the specific magnetic circuit of each instrument. In other words, while the general formulas and algorithms would remain unchanged, the numerical values of various parameters such as the longitudinal resolution ("m"), the integration length ("n") and the nonlinear LMA dependent coefficient ("A") would have to be adapted. This would involve fatigue testing a number of rope samples and calibrating the various parameters to the specific instrument.

While the invention has been described in connection with specific embodiments thereof, it will be understood that it is capable of further modifications and this application is intended to cover any variations, uses or adaptations of the invention following, in general, the principles of the invention and including such departures from the present disclo-

What is claimed is:

1. A magnetic testing device for obtaining a damage index of an elongated magnetically permeable object in real time, the device comprising:

i) a permanent magnet assembly having poles adapted to be spaced apart in the longitudinal direction of an elongated object for inducing a longitudinal magnetic flux in a section of the object between the poles of the magnet assembly, the magnet assembly being strong enough to magnetically saturate the section of the object;

ii) a tubular pole piece adapted to surround the object adjacent each pole of the permanent magnet assembly for directing the magnetic flux radially into the object at one pole and out of the object at the other pole;

iii) Hall effect devices placed in the path of the magnetic flux for sensing the reduction of the flux passing through the elongated object due to any reduction of cross-sectional area of the elongated object between the pole pieces caused by loss of metallic area in the elongated object;

iv) a leakage flux sensor installed between the pole pieces for detecting external and internal defects in the objects; and v) a real time signal processing unit for
  a) length referencing (i) local fault (LF) signals generated by the leakage flux sensor and (ii) loss of metallic area (LMA) signals generated by the Hall effect devices, by digitally sampling the LF signals and the LMA signals along the object length at preset distance intervals;
  b) summing of the standard deviations of LF signals;
  c) summing of the root-mean-square of the LF signals;
  d) integrating the absolute values of the LF signal;
  e) multiplying the LMA signal by a nonlinear coefficient dependent on the object construction and the LMA; and
  f) determining a damage index using values obtained in steps b, c, d and e, whereby a numerical damage index based on wire rope damage mechanics is obtained.

2. A monitoring device according to claim 1 wherein the damage index is determined using an equation $$D_i = A(y)y \sqrt{\sigma(x_i \ldots x_{i+m}) \int (x_i \ldots x_{i+n})^2 dx}$$

wherein

"i" is the current data point index;

"m" is the number of data points included in the longitudinal resolution of the instrument;

"n" is the number of data points included in the two-laylength integrating length;

"$D_i$" is the damage index at the location of the $i^{th}$ data point;

"$x_i$" is the $i^{th}$ LF data point;

"$y_i$" is the $i^{th}$ LMA data point;

"A(y)" is the nonlinear LMA-dependent coefficient;

"$\sigma(\ldots)$" is the standard deviation of data set; and

"$\int(\ldots)$" is the numerical integration of data set.

3. A monitoring device according to claim 2 wherein the summing of standard deviation of LF signals and the summing of the root-mean-square of the LF signals is done in a running window.

4. A monitoring device according to claim 3 wherein the running window has a length equivalent to 2–10 rope diameters.

5. A monitoring device according to claim 2 wherein the distance intervals are equivalent to 1/32 to 1 rope diameter.

6. A monitoring device according to claim 2 wherein a smoothing window comprising a set of weighing coefficients is applied on the LF data points over the integration length.

7. A monitoring device according to claim 6 wherein the integration length is 5–20 rope diameters.

8. A monitoring device according to claim 2 wherein integrating the absolute values of the LF signal is done in a running window with a length equivalent to 5–20 rope diameters, corresponding to the effective length of a broken wire.

9. A monitoring device according to claim 1 further comprising a hand-held display for displaying the damage index of the object tested.

10. A monitoring device according to claim 2 further comprising a hand-held display for displaying the damage index of the object tested.

* * * * *